United States Patent
Herms et al.

(10) Patent No.: US 6,241,972 B1
(45) Date of Patent: Jun. 5, 2001

(54) ORAL CARE FORMULATION FOR THE TREATMENT OF SENSITIVITY TEETH

(75) Inventors: James K. Herms, New York, NY (US); Gregory P. Dodd, Hackensack, NJ (US)

(73) Assignee: Block Drug Company, Inc., Jersey City, NJ (US)

( * ) Notice: Subject to any disclaimer, the term of this patent is extended or adjusted under 35 U.S.C. 154(b) by 0 days.

(21) Appl. No.: 09/253,120

(22) Filed: Feb. 19, 1999

(51) Int. Cl.$^7$ ...................................................... A61K 7/16
(52) U.S. Cl. ............................... 424/49; 424/52; 424/401
(58) Field of Search ........................... 424/49, 52, 401; 106/35

(56) References Cited

U.S. PATENT DOCUMENTS

| | | |
|---|---|---|
| 3,863,006 | 1/1975 | Hodosh . |
| 3,888,976 | 6/1975 | Mlksey et al. . |
| 3,956,480 | 5/1976 | Dichter et al. . |
| 4,057,621 | 11/1977 | Pashley et al. . |
| 4,070,510 | 1/1978 | Kahn . |
| 4,362,713 * | 12/1982 | Buck ........................ 424/54 |
| 4,380,610 * | 4/1983 | Fenton et al. ................ 525/400 |
| 4,631,185 | 12/1986 | Kim . |
| 4,634,589 | 1/1987 | Scheller . |
| 4,685,883 | 8/1987 | Jernberg . |
| 4,710,372 | 12/1987 | Scheller . |
| 4,751,072 | 6/1988 | Kim . |
| 4,960,586 * | 10/1990 | Suhonen ..................... 424/52 |
| 4,990,327 | 2/1991 | Neirinchx . |
| 4,992,258 | 2/1991 | Mason . |
| 5,188,818 * | 2/1993 | Merianos et al. ................ 424/49 |
| 5,211,939 | 5/1993 | Turesky et al. . |
| 5,240,697 | 8/1993 | Norfleet et al. . |
| 5,250,288 | 10/1993 | Turesky et al. . |
| 5,270,031 | 12/1993 | Lim et al. . |
| 5,300,290 | 4/1994 | Spencer . |
| 5,320,842 | 6/1994 | Spencer . |
| 5,374,417 * | 12/1994 | Norfleet et al. ................ 424/49 |
| 5,589,159 * | 12/1996 | Markowitz et al. ............... 424/49 |
| 5,718,885 * | 2/1998 | Gingold et al. ................ 424/49 |
| 5,800,803 * | 9/1998 | Mirajkar et al. ................ 424/54 |
| 5,885,551 * | 3/1999 | Smetana et al. ................ 424/49 |
| 6,096,292 * | 8/2000 | Halecky et al. ................ 424/49 |

FOREIGN PATENT DOCUMENTS

| | | |
|---|---|---|
| 2 227 660 | 8/1990 | (GB) . |
| WO 93 13748 | 7/1993 | (WO) . |

* cited by examiner

Primary Examiner—Ralph Gitomer

(57) ABSTRACT

A desensitizing agent for the cleaning and treatment of sensitive teeth comprising a copolymer having repeating hydrophobic and hydrophilic regions. Preferred examples include polysoaps such as: a monovalent salt of a hydrolyzed copolymer of an α-olefin and maleic anhydride:, e.g., structually represented as:

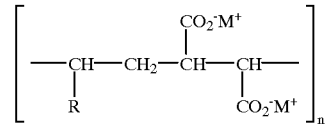

The copolymer forms micelles in aqueous dispersions such as toothpaste and mouthwash formulations. When applied thereon by brushing or rinsing or other method of application, the copolymers occlude the tubules and seal them off from the external oral environment and thereby alleviate the pain caused by the tooth's sensitivity.

10 Claims, No Drawings

ORAL CARE FORMULATION FOR THE TREATMENT OF SENSITIVITY TEETH

BACKGROUND OF THE INVENTION

1. Field of the Invention

This invention relates to compositions and methods for the treatment of pain and discomfort associated with sensitive teeth. More particularly, this invention relates to oral compositions that relieve the pain and discomfort associated with sensitive teeth.

2. Description of Related Art

Dentin is a portion of the tooth internal to the enamel and cementum that has a radially striated appearance owing to a large number of fine canals or tubules known as the dentinal tubules. Tubules run from the pulp cavity to the periphery of the dentin and are generally about two microns in diameter at their base and somewhat narrower at their periphery. Tubules are not usually exposed to the environment in the oral cavity, as they are usually covered by enamel or cementum. The cementum in turn is often covered by the gums.

While not wishing to be bound by theory, it appears that exposed tubules can lead to tooth sensitivity, an irritating and painful condition. In this theory, recession of the gum lime exposes cementum to erosion. The eroded cementum in turn exposes the hollow dentinal tubules. The exposed tubules cause nerves within the tooth to be affected excessively by external oral stimuli because material and energy transfer between the exterior and interior of the tooth is accelerated through the tubules. Common environmental stimuli, such as heat, cold, chemicals and physical and mechanical pressure or stimuli, such as brushing, are able to irritate the nerve through the open dentin tubules and thereby create pain. The pain of sensitive teeth appears to result from these stimuli, which apparently cause fluid movements in the dentinal tubules that activate pulpal nerve endings. Such pain certainly does not encourage daily oral care and treatment and so as a result those plagued with sensitive teeth do not brush as often as they should nor can they always enjoy certain foods and beverages.

Various attempts have been made in the art to cure or treat sensitive teeth so as to relieve the associated pain. One approach to relieving the pain of sensitive teeth is to reduce the excitability of the nerve in a sensitive tooth. This technique interferes with the ordinary triggering process of the nerve by altering the chemical environment of the nerve. The most well known agent for this purpose is potassium nitrate, used in commercial dentifrices for sensitive teeth and discussed in U.S. Pat. No. 3,863,006 to Hodosh, issued Jan, 28, 1975. U.S. Pat. Nos. 4,631,185 and 4,751,072 both to Kim disclose the desensitization of teeth using oral compositions comprising potassium salts such as potassium bicarbonate and potassium chloride, while U.S. Pat. No. 4,990,327 to Neirinchx describes the desensitization of teeth with strontium and fluoride ions. Other prior art methods disclose the treatment of sensitive teeth using zinc and strontium ions (U.S. Pat. No. 3,888,976 to Mlkvey et al.), and a specific blend of chloride salts (U.S. Pat. No. 3,689,686 to Svajada) Although these chemical methods of treatment provide relief in varying degrees, they are not always immediately effective.

Another approach to treating sensitivity has been to block the dentinal tubules wholly or partially with "tubule blocking agents." Tubule blocking agents can block the tubules for varying amounts of time and with varying degrees of success. The use of particulate materials as tubule blocking agents, is set forth in U.S. Pat. No. 5,718,885 to Gingold et al. for cationic alumina, U.S. Pat. No. 5,589,159 to Markowitz et al. for Laponite® clay and other hectorite clays, and in U.S. Pat. No. 4,992,258 to Mason, for montmorillonite clay. Thus prediction of beneficial tubule blocking agents is not a trivial exercise.

The use of water-soluble or water-swellable polyelectrolytes or the salts thereof as tubule blocking agents is also known. In addition, maleic acid copolymers are known to reduce the deposition of dental plaque onto teeth, with varying degrees of success, as shown in U.S. Pat. No. 4,362,713 to Buck, issued Dec. 7, 1982.

U.S. Pat. No. 4,057,021 to Pashley et al. uses oxalate salts applied to the surface of the tooth to alleviate sensitivity. Other proposed agents include various polymer systems for delivery of active agents to the teeth and gums including apatite particles (U.S. Pat. Nos. 4,634,589 and 4,710,372 to Scheller).

Along a similar vein, U.S. Pat. Nos. 5,300,290 and 5,320,842 both to Spencer disclose the use of solid polymeric particles such as polystyrene, polymethyl methacrylate, and polyvinyltoluene, among others, that have an ionically charged outer surface to which an oppositely charged antimicrobial agent such as chlorhexidine is adsorbed. The composition is used for antimicrobial action in the oral cavity in general, however, not in the treatment of sensitive teeth.

Two related patents disclose the use of similar microparticles for desensitizing teeth. U.S. Pat. No. 5,250,288, issued Oct. 5, 1993, and U.S. Pat. No. 5,211,939, issued May 18, 1993 both to Turesky et al. disclose a dentifrice comprising positively charged polystyrene particles which, it is postulated, desensitize the tooth by clinging to the surface of the teeth. The particles are intended to block the dentin tubules, thereby protecting the nerve from exposure to outside stimuli. The particles are generally from about 0.01 to 3.0 microns in diameter and may have an antimicrobial, analgesic or other therapeutic substance absorbed therein absorb thereon.

U.S. Pat. No. 5,374,417 to Norfleet al., issued Dec. 20, 1994, discloses a dentifrice for the cleaning and desensitization of sensitive teeth consisting of a standard toothpaste base or carrier containing the potassium salt of a synthetic anionic polycarboxylate polymer as the desensitizing agent. The polycarboxylate polymer particles apparently enter the dentinal tubules during brushing, and their penetration blocks the tubules and prevents physical, chemical and/or osmotic stimulation of the nerves.

U.S. Pat. No. 5,188,818 to Merianos et al., issued Feb. 23, 1993, discloses a dentifrice comprising about 0.1% to 20% of a strontium salt of a maleic anhydride/methyl vinyl ether copolymer as a desensitizer. The carrier base consists of the standard surfactants, humectants, thickeners, anti-caries agents and flavors as is known in the art.

U.S. Pat. No. 5,270,031 to Lim et al., issued Dec. 14, 1993, discloses oral compositions for relieving the pain and discomfort of sensitive teeth, consisting of water-soluble or water-swellable polyelectrolyte salts. The polyelectrolyte salts can comprise the anionic, cationic or amphoteric forms of methyl vinyl ether and maleic anhydride copolymers or polyacrylic acid polymers with sodium, calcium, potassium, ammonium, zinc and other similar metals.

Dentin sensitivity is, of course, not the only problem that can arise in the mouth, and polymers have long been known for various dental applications. U.S. Pat. No. 4,685,883 to Jernberg discloses the use of biodegradable microspheres to deliver chemotherapeutic agents to treat periodontal disease. U.S. Pat. No. 3,956,480 to Dichter et al., issued May 11, 1976, describes and claims the treatment of teeth with anionic polymers that are complexed with a cationic antimicrobial agent such as chlorhexidine.

However, in order for any of the aforementioned compositions to be effective as a tubule blocker, thereby reducing the pain and discomfort of sensitive teeth, they must not only be able to block the tubule once inside the tubule, but they must also be able to enter the tubule in the first place. Tubules of sensitive human dentin may contain organic material that prevents the bulk movement of certain materials into the tubules. Additionally, evidence has shown a continuous outward flow of fluid when vital dentin is exposed and the dentinal smear layer is removed. This outward fluid flow from the tubules could counteract the ability of any desensitizing materials to enter the tubules for blockage of fluid movement. The mere application of such materials with a toothbrush (as a paste) or in solution (as a mouthwash) would not necessarily generate sufficient force to drive the desensitizing materials into the tubules of live, sensitive dentin. Hence, the need exists for desensitizing compositions that have an affinity for the tubule interior and the outer regions of the tubule so as to insure a desensitizing effect.

SUMMARY OF THE INVENTION

The principal object of the present invention therefore is to provide a tubule blocking agent that is useful as a desensitizer and compatible with typical dentifrice and mouthrinse ingredients.

It is an additional object of the invention to provide a desensitizer that can migrate to the entrance of a tubule easily and that will remain in the tubule, blocking the tubule at least partially, for some time after application.

It is an advantage of the invention that the desensitizing agent is nontoxic and organoleptically acceptable. It is an additional advantage of the invention that the desensitizing agent does not adversely affect the qualities of the dentifrice or mouthrinse and does not coat the teeth or tongue so thickly as to detract from the cleansing sensation of conventional dentifrices.

It is still another advantage of the invention that the presence of the desensitizing agent does not interfere with conventional manufacturing and processing of dentifrices. It does not require unusual steps such as high-shear homogenization to manufacture a dentifrice containing this desensitizer.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a desensitizing agent comprising closely spaced hydrophilic and hydrophobic regions.

To further achieve the foregoing objects and in accordance with the purpose of the invention, the invention further provides a method for treating dentinal sensitivity by administering a desensitizing agent comprising closely spaced hydrophilic and hydrophobic regions to an affected tooth.

DETAILED DESCRIPTION OF THE INVENTION

Reference will now be made to the preferred embodiments of the invention. These embodiments, however, illustrate the invention and the principles of the invention. The embodiments and examples set forth herein are not intended to limit the scope or spirit of the invention.

The desensitizer of the invention may be any material capable of blocking dentin tubules and having closely associated hydrophilic and hydrophobic regions. While certain polymers and copolymers are primarily contemplated as being within the invention, nonpolymeric materials may incorporate the principles of operation of the invention set forth below.

The desensitizing agent of the invention is preferably a polymer. As used herein, "polymer" is intended to encompass both homopolymers and copolymers. Copolymers may include alternating copolymers, random copolymers, statistical copolymers, graft copolymers and block copolymers. Preferably, the polymer of the invention is a homopolymer or an alternating copolymer, and more preferably an alternating copolymer. The polymer of the invention may be linear or branched or even crosslinked to form a network polymer. Without wishing to be bound by theory, it appears that the desensitizing agent of the invention may increase the hydrodynamic resistance of the dentin without increasing the hydrodynamic resistivity (viscosity) of the residual fluid in the mouth. To accomplish this result, it appears that the polymer of the invention must have closely spaced hydrophobic and hydrophilic regions. The desensitizing agent should be sufficienly hydrophilic to form micelles, yet sufficiently hydrophobic to retain effectiveness in use.

As stated above, the desensitizing agent of the invention is preferably a polymer, more preferably a copolymer, having closely adjacent hydrophobic and hydrophilic regions. More preferably, the copolymers have at least one hydrophilic monomer capable of forming a salt, and most preferably, the copolymer comprises a monovalent cation salt of a hydrophobic/hydrophilic copolymer that disperses into micelles in aqueous systems. The hydrophobic monomer is preferably a long chain $\alpha$-olefin while the hydrophilic monomer is preferably a strongly hydrophilic monomer that causes its associated copolymer form to create micelles. Preferred hydrophilic monomers are highly hydrophilic salt-forming monomers, such as carboxylic acids and diacids. Most highly preferred hydrophilic monomers are diacids, such as maleic acid. Other anionic polymeric salts may also be used. Preferably, the copolymer is a regular copolymer that alternates between the two types of monomers in the copolymer chain. Blockier copolymers are also acceptable, but not preferred. The desensitizing agent of the invention apparently plugs the dentinal tubules without coating the teeth or tongue so as to detract from the cleaning sensation desired with conventional toothpastes.

The desensitizing active agent of the present invention is preferably a polysoap i.e., the salt of a copolymer consisting of different, alternating monomeric subunits. One monomer is highly hydrophobic and preferably is a long chain $\alpha$-olefin comprising a carbon chain of at least about eight (8), preferably at least about ten (10) and more preferably at least about twelve (12) carbon atoms. The second monomer is hydrophilic in character and preferably consists of a maleic acid or anhydride moiety. Generally, the agent can be structurally represented as follows:

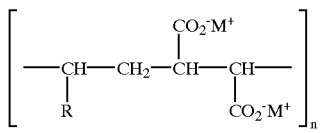

which is repeated any number of times (i.e., wherein $n \geq 2$) to produce the copolymer. R is a long chain aliphatic group comprised of a higher alkyl group, for example a hexyl group ($C_6H_{13}$) or an octyl ($CH_8H_{17}$) or longer group and $M^+$ is a monovalent cation, preferably sodium, potassium, ammonium, choline, lysine, triethanolamine and mixtures thereof. The active desensitizing agent can comprise of any number of repeating monomeric units, but preferably the hydrophobic/hydrophilic copolymer will have a molecular weight of from about 2,000 to about 1,000,000 daltons, preferably about 5,000 to about 500,000 daltons and most preferably about 10,000 to about 100,000 daltons.

More preferably, the copolymer is the hydrolysis product of an alternating long chain α-olefin-co-maleic anhydride copolymer wherein the α-olefin has at least about ten carbons and even more preferably at least about twelve carbons (e.g., $C_{12}H_{24}$) or higher. Suitable copolymers of this nature include tetradecene/maleic anhydride copolymer, octadecene/maleic anhydride copolymer, triacontene/maleic anhydride copolymer and mixtures thereof. An especially preferred desensitizing agent is Chevron/Gulf PA-18 brand Polyanhydride Resin, an alternating copolymer of a 1:1 molar ratio of maleic anhydride and 1-octadecene (CAS: "1-octadecene polymer with 2,5-furandione"; INCA: octadecene/MA copolymer). The resin has an average molecular weight from about 10,000 to about 60,000 daltons. Even more preferred is the hydrolyzed cation salt of the copolymer, especially the monovalent salts thereof. It has been reported that the polyvalent cations added to monovalent salts of PA-18 resins can cause precipitation of aqueous solutions of the monovalent cation salt. Thus, monovalent salts are preferred for handling characteristics. Especially preferred monovalent salts are the alkali salts and most preferably the sodium or potassium salts thereof and the monovalent cations of ammonium, triethanolamine, choline and lysine. The degree of substitution of the salt may also affect the desensitizing properties of the material. A higher degree of substitution will generally increase the hydrophilic properties of the material.

The preferred resin, PA-18, is insoluble in raw form and is made water soluble or dispersible by hydrolyzing the resin with aqueous sodium hydroxide to form the disodium salt of the polymer. Full hydrolysis is not, however, necessary.

Alternatively, the desensitizing agent of the present invention may comprise a hydrophobic/hydrophilic oligomer such as a maleic modified rosin ester. In either case, it is important that the copolymer readily disperses in aqueous solutions and forms micelles when so dispersed. It is also important as pointed out earlier that the polymer be compatible with the other conventional dentifrice ingredients that make up the remainder of the toothpaste formulation.

The desensitizing dentifrice compositions of the present invention utilize many conventional toothpaste ingredients in order to clean the teeth and help prevent cavities and gum disease while at the same time incorporating a novel desensitizing agent for the alleviation of pain in those suffering from sensitive teeth. The desensitizing agent is not only compatible within conventional toothpaste and mouthwash formulations, but exhibits an affinity for the dentinal tubules and orifices. Thus, the desensitizer occludes and blocks it, thereby preventing irritation of the nerves within the pulpal cavity by physical stimuli, heat, cold or chemicals. The blockage of the tubules also impedes the subsequent transmission of pressure gradients through the dentin as well as the possible invasion of bacteria and other microbes from the oral cavity.

The desensitizing copolymer compounds are incorporated in the tooth paste formulations in an amount of from about 0.5% to about 15.0%, preferably from about 2% to about 10%, more preferably from about 3% to about 8% and most preferably about 6% by weight of a dentifrice formulation.

Other conventional toothpaste ingredients may be incorporated in the inventive formulations as follows.

Thickeners useful in the toothpaste formulations of the present invention include natural and synthetic gums, hydrocolloids, cellulose derivatives, silicates and the like. These include hydrated silicas, silicates, colloidal silica, sodium carboxymethyl cellulose, polyvinyl pyrrolidone, methyl cellulose, hydroxy propyl methyl cellulose, xanthan gum, hydroxyethyl cellulose, carrageenan and mixtures thereof as is known in the art. Preferably, the thickener is hydrated silica, colloidal silica and mixtures thereof, while the binder employed is a cellulose derivative such as hydroxyethyl cellulose.

Humectants such as glycerol, sorbitol, polyethylene glycol and mixtures thereof may be added to stabilize the composition and act as a carrier to maintain and stabilize the active.

The surface active agent or surfactant will normally be a water soluble detergent that is useful to clean the teeth (and gums). Such detergents have useful foaming properties. The organic surface-active material is preferably anionic, non-ionic or ampholytic in nature, and most preferably is anionic. Suitable examples of anionic surfactants are higher alkyl sulfate and their salts such as an alkali or other suitable salt of lauryl sulfate, higher fatty acid monoglyceride monosulfates, such as the alkali or other suitable salt of the monosulfated monoglyceride of hydrogenated coconut oil fatty acids, alkyl aryl sulfonates such as an alkali or other suitable salt of dodecylbenzene sulfonate, higher fatty sulfoacetates, higher fatty acid esters of 1,2 dihydroxypropane sulfonate, and the higher aliphatic acyl amides of lower aliphatic amino carboxylic acid compounds, such as those having 12 to 16 carbons in the fatty acid, and the like. Examples of the last mentioned amides are N-lauroyl sarcosine, and the alkali salts of N-lauroyl or N-palmitoyl sarcosine.

Examples of water soluble nonionic surfactants are condensation products of ethylene oxide with various hydroxyl-containing compounds that are reactive therewith and have long hydrophobic chains (e.g., aliphatic chains of about 12 to 20 carbon atoms), which condensation products ("poloyxamers or ethoxylates") contain hydrophilic polyethylene oxide moieties, such as condensation products, poly (ethylene oxide) with fatty acids, fatty alcohols, fatty amides and other fatty moieties, and with propylene oxide and polypropylene oxides (e.g., Pluronic materials).

Of the mentioned detergents the higher fatty alcohol sulfates are preferred (in such detergents and in the other detergents mentioned, and elsewhere in this specification "higher", when employed in designating alkyl groups, fatty acids, etc., identifies such as containing 10 to 20 carbon atoms, preferably 12 to 18, which preferably are in linear arrangement). Anionic surfactants such as sodium lauryl sulfate or sodium lauroyl sarcosinate are preferred as they also act as foaming agents within the formulation. The polishing agents of the toothpaste bases are water insoluble materials which are sometimes referred to as abrasives. Preferred polishing agents are siliceous materials such as silica, and will normally be of fine particles, such as those of a mean particle size up to about 10 microns and of a very high surface/volume ratio, which may be as much as 250 square meters/gram. A preferred silica is a precipitated amorphous hydrated silica, such as Zeodent 113 or 115, marketed by J.M.Huber Corporation, but other polishing agents may be employed too, including water-insoluble sodium metaphosphate, potassium metaphosphate, tricalcium phosphate, calcium phosphate dihydrate, anhydrous dicalcium phosphate, calcium pyrophosphate, magnesium orthophosphate, calcium carbonate trihydrate, alumina trihydrate, aluminum silicate, zirconium silicate, calcined alumina, bentonite, silica gel or colloidal silica, and complex amorphous alkali metal aluminosilicates and mixture thereof. Still other suitable polishing materials include the particulate thermosetting resins described in U.S. Pat. No. 4,070,510, such as melamine-, phenolic-, and urea-formaldehyde, and crosslinked polyepoxides and polyesters.

Anticaries agents such as stannous fluoride, sodium and potassium fluoride, sodium and potassium monofluorophosphate and the like may be incorporated in the dental compositions in amounts and in ways well known in the art. The fluoride compositions not only help in the prevention of cavities but also contribute to the strengthening of the enamel surface.

Other excipients may be added to the toothpaste formulations of the present invention as is known in the art, and these include anti-tartar and anti-calculus compounds such as sodium and potassium pyrophosphate salts and zinc oxide. Conventional sweeteners may also be added such as saccharin, aspartame, acesulfame-K, sucralose, cyclamates and the like. Flavors such as peppermint, spearmint, menthol, wintergreen and the like as well as FDA-approved food dyes as colorants may also be added for a more pleasant taste and visual effect.

Known desensitizing agents may also be incorporated into the invention, including agents such as potassium nitrate, potassium chloride, potassium bicarbonate and strontium chloride. Other tubule blocking agents may also be added to formulations comprising the invention.

The desensitizer of the invention is preferably used in a dentifrice, although other systems, such as mouthrinses, oral gels and other delivery systems, are also acceptable. Such dentifrices may employ a vehicle or base for maintaining and stabilizing the active ingredients contained therein, thickeners, anti-caries agents, surfactants, humectants, sweeteners, flavor oils, foaming agents, abrasives, anti-tartar agents, gums, stabilizers, colorants and the like. The vehicle or base normally comprises water, a humectant, detergent and polishing agent or abrasive.

The following examples are provided in order to more fully describe and detail particular embodiments and formulations comprising the compositions of the present invention. They are for illustrative purposes only, and it is understood that minor changes and alterations can be made to these formulations and the processes for their preparation that are not contemplated thereby. It should be understood that to the extent any such changes do not materially alter the final product or its process said changes are contemplated herein as falling within the spirit and scope of the invention as recited by the claims that follow.

EXAMPLE 1

A toothpaste composition was prepared using the formulation set forth in Table 1. The desensitizing agent is the sodium salt of an octadecene/maleic anhydride copolymer. The weight percent given for each ingredient is based on a value of 100% for the total formulation.

TABLE 1

Dentifrice Formulation of Example 1

| Ingredient | Weight % |
| --- | --- |
| Water | 51.0 |
| Octadecene Maleic Anhydride copolymer | 6.0 |
| Sodium hydroxide | 1.3 |
| Sodium lauroyl sarcosinate | 0.4 |
| Sodium saccharin | 0.3 |
| Sodium fluoride | 0.2 |
| Phosphoric acid | 0.2 |
| Hydroxyethylcellulose | 2.3 |
| Hydrated silica abrasive | 6.0 |
| Sodium lauryl sulfate | 1.2 |
| Glycerin | 23.0 |
| Hydrated silica thickener | 8.0 |
| Methyl salicylate | 0.1 |
| Total | 100.0 |

The water, copolymer and hydroxide were heated at 85° C. and stirred for 45 min. to form the water-soluble or dispersible tubule blocking agent. The sarcosinate, saccharin, fluoride and acid were then stirred in. After cooling, the binder and abrasive were blended in under vacuum for 30 min. The lauryl sulfate, glycerin and thickener were then blended in, under vacuum, for another 30 min. Finally the flavor oil was blended in.

In order to evaluate the potential activity of this composition as a desensitizing dentifrice, it was brushed onto a dentin disc using the method of Pashley (set forth in Spangberg, "Experimental Endodontics," CRC Press, 1989, incorporated herein by reference), with modifications as described in U.S. Pat. No. 5,589,159 to Markowitz et al. (incorporated herein by reference). The result was a reduction in hydraulic conductance, $\Delta Lp$, of $-92\%$.

These results confirm that this dentifrice has the potential to radically reduce intradentinal fluid flow, by tubule occlusion and blockage.

EXAMPLE 2

A second toothpaste formulation was prepared comprising a disodium salt of hydrolyzed octadecene/maleic anhydride copolymer (i.e., disodium octadecene/maleate copolymer) as a desensitizing agent. The the process of preparation was the same as that set forth in Example 1. The formulation is set forth in Table 2. This composition can be processed at lower temperatures than the dentifrice of Example 1 (e.g., 60° C.).

TABLE 2

Formulation of Example 2

| Ingredient | Weight % |
| --- | --- |
| Water | 51.6 |
| Octadecene Maleic Anhydride copolymer hydrolyate (disodium salt) | 6.7 |
| Sodium lauroyl sarcosinate | 0.4 |
| Sodium saccharin | 0.3 |
| Sodium fluoride | 0.2 |
| Phosphoric acid | 0.2 |
| Hydroxyethylcellulose | 2.3 |

TABLE 2-continued

Formulation of Example 2

| Ingredient | Weight % |
| --- | --- |
| Hydrated silica abrasive | 6.0 |
| Sodium lauryl sulfate | 1.2 |
| Glycerin | 23.0 |
| Hydrated silica thickener | 8.0 |
| Methyl salicylate | 0.1 |
| Total | 100.0 |

EXAMPLE 3

The desensitizing agent of the invention was formulated as an oral mouthwash composition using the ingredients set forth in Table 3. The components were mixed following generally acceptable pharmaceutical procedures for mouthwash compositions.

The Pashley method of Example 1 was again followed in order to determine the composition's ability to affect or reduce intra-dentinal fluid flow. The composition produced a reduction in hydraulic conductance, $\Delta Lp$, of $-92\%$ following irrigation of the disk with the experimental mouthwash, indicating a significant decrease in intradentinal fluid flow. Hence, use of the desensitizing agents in mouthwash compositions will also result in dentinal tubule occlusion and the reduction in tooth sensitivity.

TABLE 3

Formulation of Example 3

| Ingredient | Weight % |
| --- | --- |
| Water | 75.9 |
| Octadecene Maleic Anhydride copolymer | 6.0 |
| Potassium hydroxide | 1.4 |
| Sodium saccharin | 0.1 |
| Sodium fluoride | 0.1 |
| Sodium chloride | 0.4 |
| Propylene glycol | 8.0 |
| Glycerin | 8.0 |
| Thymol + menthol | 0.1 |
| Total | 100.0 |

EXAMPLE 4

A desensitizing solution was prepared according to the formulation set forth in Table 4. When tested using the method of Example 1, the composition produced a reduction in hydraulic conductance, $\Delta Lp$, of $-88\%$, when tested as in Example 3.

TABLE 4

Formulation of Example 4

| Ingredient | Weight % |
| --- | --- |
| Water | 87.2 |
| Tetradecene Maleic Anhydride copolymer | 6.0 |
| Potassium hydroxide | 1.6 |
| Sodium fluoride | 0.2 |
| Glycerin | 5.0 |
| Total | 100.0 |

EXAMPLE 5

A desensitizing solution was prepared using the ingredients set forth in Table 5 in their respective amounts. The composition produced a reduction in hydraulic conductance, $\Delta Lp$, of $-80\%$, using the method of Example 3.

TABLE 5

Formulation of Example 5

| Ingredient | Weight % |
| --- | --- |
| Water | 87.9 |
| Triacontene Maleic Anhydride copolymer | 6.0 |
| Potassium hydroxide | 0.9 |
| Sodium fluoride | 0.2 |
| Glycerin | 5.0 |
| Total | 100.0 |

EXAMPLE 6

A dentifrice was prepared as in Example 1. The formulation is set forth in Table 6. This dentifrice proved to have acceptable physical characteristics in accordance with the invention.

TABLE 6

Formulation of Example 6

| Ingredient | Weight % |
| --- | --- |
| Deionized Water | 44.29 |
| Potassium hydroxide | 1.70 |
| PA-18 resin | 6.00 |
| Hydrochloric acid (3N) | 1.00 |
| Sodium saccharin | 0.27 |
| Sodium fluoride | 0.24 |
| Hydroxyethyl cellulose (Natrosol 250M) | 1.70 |
| Abrasive silica (Zeodent 113) | 6.00 |
| Thickening silica (Zeodent 165) | 5.00 |
| Fatty acid amidoalkyl betaine (TEGO-betain ZF (30% solution)) | 5.00 |
| Glycerin (96%) | 13.00 |
| Sorbitol Solution (70%) | 15.00 |
| Flavor | 0.80 |
| Total | 100.00 |

EXAMPLE 7

A dentifrice was prepared as in Example 1. The formulation is set forth in Table 7. This dentifrice proved to have acceptable physical characteristics in accordance with the invention.

TABLE 7

Formulation of Example 7

| Ingredient | Weight % |
| --- | --- |
| Deionized Water | 37.96 |
| Sodium hydroxide | 1.20 |
| PA-18 resin | 4.00 |
| Hydrochloric acid (3N) | 1.00 |
| Sodium saccharin | 0.20 |
| Sodium fluoride | 0.24 |
| Hydroxyethyl cellulose (Natrosol 250M) | 1.80 |
| Abrasive silica (Tixosil 73) | 4.00 |
| Abrasive silica (Sylodent 756) | 3.00 |

TABLE 7-continued

Formulation of Example 7

| Ingredient | Weight % |
|---|---|
| Polyethylene (Luvitol 12M) | 4.00 |
| Fatty acid amidoalkyl betaine (TEGO-betaine ZF (30% solution)) | 3.00 |
| Glycerin (96%) | 37.90 |
| Titanium dioxide | 0.70 |
| Flavor | 1.00 |
| Total | 100.00 |

EXAMPLE 8

A dentifrice was prepared as in Example 1. The formulation is set forth in Table 8. This dentifrice proved to have acceptable physical characteristics in accordance with the invention.

TABLE 8

Formulation of Example 8

| Ingredient | Weight % |
|---|---|
| Deionized water | 48.04 |
| Sodium hydroxide | 1.05 |
| PA-18 resin | 6.00 |
| Sodium saccharin | 0.27 |
| Sodium fluoride | 0.24 |
| Polaxamer (Pluronic 127) | 0.80 |
| Hydroxyethyl cellulose (Natrosol 250M) | 1.20 |
| Sodium carboxymethyl cellulose (type 12M8P) | 0.50 |
| Abrasive silica (Zeodent 113) | 6.00 |
| Thickening silica (Zeofree 153) | 11.00 |
| Sodium lauryl sulfate (30% solution) | 3.00 |
| Glycerin (96%) | 6.00 |
| Sorbitol solution (70%) | 14.00 |
| Titanium dioxide | 0.70 |
| Flavor | 1.20 |
| Total | 100.00 |

EXAMPLE 9 (INVENTIVE) AND EXAMPLE 10 (COMPARATIVE)

Dentifrice formulations were prepared with the formulations shown in Table 9. The hydraulic conductance of the formulations was measured as set forth in Example 1, after brushing. The results are set forth in Table 10.

TABLE 9

Formulations of Examples 9 and 10

| Ingredient | Weight Percent Ex. 9 | Weight Percent Ex. 10 |
|---|---|---|
| Purified water | 46.387 | 53.187 |
| Sodium Hydroxide | 1.1 | 0 |
| Polyanhydride Resin (PA-18) | 6.0 | 0 |
| Sodium Fluoride | 0.243 | 0.243 |
| Sodium Saccharin | 0.270 | 0.270 |
| Polyoxil 40 Stearate | 1.5 | 1.5 |
| Titanium Dioxide | 0.7 | 0.7 |
| Xantham Gum | 0.5 | 0.8 |
| Hydroxyethyl Cellulose | 1.2 | 1.2 |
| Zeodent 113 | 10.0 | 10.0 |
| Zeofree 153 | 10.0 | 10.0 |
| Sorbitol Solution | 14.0 | 14.0 |
| Glycerin | 6.0 | 6.0 |
| Sodium Lauryl Sulfate | 0.9 | 0.9 |
| Peppermint Oil | 0.816 | 0.816 |
| Menthol | 0.252 | 0.252 |
| Anethole | 0.132 | 0.132 |
| Total | 100 | 100 |

TABLE 10

Hydraulic Conductance of Examples 9 and 10

| Conductance, ΔLp | Example 9 | Example 10 |
|---|---|---|
| Post-Brush | −91 | −29 |

It will be apparent to those skilled in the art that various modifications may be made to the examples and the matters described herein without departing from the scope or spirit of the invention.

What is claimed is:

1. A dentifrice composition for treating sensitive teeth, comprising, as a desensitizing agent, a member selected from the group consisting of copolymers having repeated units of a hydrophilic monomer and a hydrophobic monomer consisting of an α-olefin having from 12 to 30 carbon atoms, full and partially hydroylzed forms thereof and full or partial salts thereof.

2. The composition of claim 1, wherein said desensitizing agent is selected from the group consisting of tetradecene/maleic anhydride copolymer, octadecene/maleic anhydride copolymer and triacontene/maleic anhydride copolymer.

3. The composition of claim 1, wherein said hydrophilic monomer is a salt-forming monomer selected from the group consisting of carboxylic acids, dicarboxylic acids, dicarboxylic acid anhydrides, esters of carboxylic acids and esters of dicarboxylic acids.

4. The composition of claim 3, wherein said hydrophilic monomer is selected from the group consisting of maleic acid, maleic anhydride, and salts thereof.

5. The composition of claim 1, wherein said desensitizing agent is a cation salt of said fully or partially hydrolyzed copolymer.

6. The composition of claim 5, wherein said salt is a monovalent cation salt selected from the monovalent cations of sodium, potassium, ammonia, triethanolamine, choline, lysine and mixtures thereof.

7. The composition of claim 1, wherein said copolymner has an average molecular weight from about 10,000 to about 60,000 daltons.

8. The composition of claim 1, wherein said desensitizing agent comprises from about 0.5% to about 15% of said dentifrice.

9. The composition of claim 8, wherein said desensitizing agent comprises from about 2% to about 10% by weight of said dentifrice composition.

10. The composition of claim 1, further comprising thickeners, anti-caries agents, surfactants, anti-tartar agents, humectants, flavor oils, sweeteners, foaming agents, water, abrasives, binders, stabilizers, colorants, and mixtures thereof.

* * * * *